(12) United States Patent
Han et al.

(10) Patent No.: US 11,921,123 B2
(45) Date of Patent: Mar. 5, 2024

(54) QUANTITATIVE DETECTION METHOD OF RARE EARTH DOPED CALCIUM PHOSPHATE FLUORESCENT NANOPARTICLES IN ORGANISMS

(71) Applicant: WUHAN UNIVERSITY OF TECHNOLOGY, Hubei (CN)

(72) Inventors: Yingchao Han, Hubei (CN); Qingguo Xing, Hubei (CN); Xinyu Wang, Hubei (CN)

(73) Assignee: WUHAN UNIVERSITY OF TECHNOLOGY, Hubei (CN)

( * ) Notice: Subject to any disclaimer, the term of this patent is extended or adjusted under 35 U.S.C. 154(b) by 1061 days.

(21) Appl. No.: 16/356,250

(22) Filed: Mar. 18, 2019

(65) Prior Publication Data

US 2020/0200777 A1    Jun. 25, 2020

(30) Foreign Application Priority Data

Dec. 21, 2018 (CN) .......................... 201811572579.3

(51) Int. Cl.
| | | |
|---|---|---|
| *G01N 33/94* | (2006.01) | |
| *G01N 21/64* | (2006.01) | |
| *G01N 33/483* | (2006.01) | |
| *G01N 33/58* | (2006.01) | |
| *G01N 33/84* | (2006.01) | |

(52) U.S. Cl.
CPC .......... *G01N 33/94* (2013.01); *G01N 21/6428* (2013.01); *G01N 33/4833* (2013.01); *G01N 33/587* (2013.01); *G01N 33/84* (2013.01); *G01N 2021/6439* (2013.01)

(58) Field of Classification Search
CPC .............. G01N 33/94; G01N 21/6428; G01N 33/4833; G01N 33/587; G01N 33/84; G01N 2021/6439

USPC ....................................................... 435/40.52
See application file for complete search history.

(56) References Cited

U.S. PATENT DOCUMENTS 8,906,415 B1 * 12/2014 Bhaduri ............... A61K 9/5115
424/489

FOREIGN PATENT DOCUMENTS

| CN | 103822906 A | 5/2014 |
|---|---|---|
| CN | 105018086 A | 11/2015 |
| CN | 107573938 A | 1/2018 |

OTHER PUBLICATIONS

Lebugle et al., Colloidal and monocrystalline Ln3+ doped apatite calcium phosphate as biocompatible fluorescent probes, Chemical Communications, (2006), pp. 606-608.*

* cited by examiner

*Primary Examiner* — Jennifer M. H. Tichy
(74) *Attorney, Agent, or Firm* — Tim Tingkang Xia, Esq.; Locke Lord LLP (57) ABSTRACT

A quantitative detection method of rare earth doped calcium phosphate fluorescent nanoparticles (RE-nCaP) in organisms includes establishing a fluorescent intensity-concentration standard curve of rare earth ions, preparing samples to be tested and the blank control group into homogenate, performing centrifuging and testing the fluorescent intensity of supernatants, calculating the fluorescent intensity values per unit mass or volume of the samples and the blank control group, and performing significant difference analysis; if P is greater than or equal to 0.05, determining that the RE-nCaP content in the samples is 0, and if P is smaller than 0.05, testing the tissue extraction rate of RE-nCaP; and comprehensively considering the tissue extraction rate, the homogenate volume, the fluorescent intensity value per until mass or volume, the homogenate dilution ratio, and the doping amount to obtain the accurate content of the RE-nCaP in biological tissue samples.

7 Claims, 7 Drawing Sheets

QUANTITATIVE DETECTION METHOD OF RARE EARTH DOPED CALCIUM PHOSPHATE FLUORESCENT NANOPARTICLES IN ORGANISMS

CROSS-REFERENCE TO RELATED APPLICATION

This application claims priority to Chinese Patent Application No. 201811572579.3, filed Dec. 21, 2018 in the State Intellectual Property Office of P.R. China, which is hereby incorporated herein in its entirety by reference.

FIELD OF THE INVENTION

The invention relates to the technical field of biological detection, in particular to a quantitative detection method of rare earth doped calcium phosphate fluorescent nanoparticles in organisms. The method can be used for studying the biodistribution and metabolism process of fluorescent nanoparticles in the organisms.

BACKGROUND OF THE INVENTION

Calcium phosphate is a main component of hard tissues (bones, teeth and the like) of a human body, and mainly comprises amorphous calcium phosphate (ACP), dicalcium phosphate dehydrate (DCPD), octocalcium phosphate (OCP), hydroxylapatite (HAP) and the like. The calcium phosphate has favorable biological compatibility and biological activity, and has been widely applied in the biomedicine field. Nanometer calcium phosphate shows favorable application potential in the respects of pharmaceutical carriers, inorganic phases of biocomposite, nanometer bioceramics and the like due to advantages of small size, high specific surface area, high adsorption capacity, high biological activity, high osteogenesis capacity and the like. In addition, considering the fluorescence and the magnetism of rare-earth elements, rare earth doped calcium phosphate nanoparticles hopefully become a biocompatible and biodegradable fluorescent or magnetic imaging agent used for diagnosing diseases. The distribution and metabolism of rare earth doped calcium phosphate as a biological imaging agent in organism tissues is necessary to be studied.

At present, a technique for in vivo tracing study of calcium phosphate nanoparticles mainly includes a radioisotope labelling method and a fluorescent macromolecule labelling method. The radioisotope labelling method has the advantages of being high in detection sensitivity and the like, but the method needs to be performed under the stringent professional condition, and radioactive isotopes have potential safety risk on the organisms. According to the fluorescent macromolecule labelling method, generally, fluorescent macromolecules are adhered to the surfaces of the calcium phosphate nanoparticles through physical adsorption or chemical bonding, so that better tracing effects can be achieved at the early stage, but along with dissolution of the calcium phosphate nanoparticles, the fluorescent macromolecules will be separated from the calcium phosphate to lose labelling effects, and therefore long-term in vivo tracing effects cannot be achieved.

Earlier, the inventor team discloses a preparation method of rare earth doped calcium phosphate fluorescent nanoparticles (RE-nCaP) (CN105018086A) and a quantitative detection tracing method for hydroxylapatite (HAP) nanoparticles in cells (CN103822906A). The method can accurately reflect the dissolution situation of the hydroxylapatite nanoparticles in the cells and perform quantitative detection on the hydroxylapatite nanoparticles, but a blank control group is not set for significant difference analysis, and the extraction rate of rare-earth elements in biological tissues is not calculated either, so that the accuracy needs to be strengthened. In addition, the method cannot detect the content of rare earth doped calcium phosphate in animal tissues (including hard tissues, soft tissues and blood) and metabolites (urine and excrement) accurately and quantitatively.

Based on the preparation method of the RE-nCaP and the quantitative detection tracing method for the HAP nanoparticles in the cells, through continuous deep study, the inventor team develops a new quantitative detection method. According to the method, the detection limit concentration can reach 0.1 nM, the content of the RE-nCaP in the organisms (including hard tissues, soft tissues and blood) and biological metabolites can be precisely detected, and a precise detection method can also be provided for studying distribution, metabolism and the like of the nanoparticles in the organisms.

SUMMARY OF THE INVENTION

The invention aims to provide a quantitative detection method of RE-nCaP in organisms.

The method comprises the following steps:
(a) establishing a fluorescent intensity-concentration standard curve of rare earth (RE) ions in a fluorescent enhancement liquid system;
(b) separately treating biological tissue samples in a group to be tested, and biological tissue samples excluding RE-nCaP in a blank control group through an acid solution to obtain homogenates of the group to be tested and the blank control group, taking an appropriate amount of the homogenates of the group to be tested and the blank control group, performing centrifugal separation to obtain supernatants, diluting the supernatants with fluorescent enhancement liquid, detecting the fluorescent intensity of the diluted supernatants, performing significant difference analysis on the fluorescent intensity value of the diluted supernatant per unit mass or volume between the group to be tested and the blank control group, if significant difference does not exist between the fluorescent intensity value of the diluted supernatant per unit mass or volume in the group to be tested and the fluorescent intensity value of the diluted supernatant per unit mass or volume in the blank control group (P is greater than or equal to 0.05), indicating that the biological tissue samples in the group to be tested do not contain RE-nCaP (namely that the content is 0), performing ending at the time without performing subsequent operations, and if the significant difference exists between the fluorescent intensity value of the diluted supernatant per unit mass or volume in the group to be tested and the fluorescent intensity value of the diluted supernatant per unit mass or volume in the blank control group (P is smaller than 0.05), further determining the content of the RE-nCaP in the biological tissue samples of the group to be tested according to operations in a step (c) and a step (d);
(c) separately adding the RE-nCaP to the homogenate in the blank control group and the acid solution having the same volume as that of the homogenate, performing centrifugal separation to obtain supernatants, diluting the supernatants with the fluorescent enhancement liquid, detecting the fluorescent intensity of the diluted supernatants, calculating the tissue retention rate per unit weight or volume according to the fluorescent intensity of the homogenate in the blank control group and the fluorescent intensity of the acid solution, and further calculating the tissue extraction rate in the group to be tested according to the mass or the volume of biological tissues in the group to be tested; and (d) comprehensively considering the fluorescent intensity-concentration standard curve, the tissue extraction rate, the homogenate volume, the fluorescent intensity value per unit mass or volume, the dilution ratio and the mole content of rare earth elements in calcium phosphate, and finally calculating the content of RE-nCaP in the biological tissue samples in the group to be tested.

According to the above scheme, an establishing method of the standard curve of the fluorescent intensity y and the concentration x in the step (a) specifically comprises the following steps: by using the fluorescent enhancement liquid as a solvent, preparing a series of rare earth ion standard solutions having different concentrations (7 nmol/L or below), determining the fluorescent intensity of the rare earth ion standard solutions at the specific emission wavelength (for example, $Eu^{3+}$ is 618 nm or $Tb^{3+}$ is 488 nm) under the specific excitation wavelength (330-350 nm, preferably 340 nm) through a fluorescent spectrophotometer, and performing straight-line fitting so as to obtain a relationship between the fluorescent intensity y and the concentration x: y=B+Nx, wherein B is intercept (cps), and N is slope (cps/(nmol/L)).

According to the above scheme, the step (b) comprises the specific processes: accurately measuring the mass or the volume of the biological tissue samples in the group to be tested and the mass or the volume of the biological tissue samples excluding Eu-nCaP in the blank control group separately, then adding the acid solution to obtain the homogenate in the group to be tested and the homogenate in the blank control group, taking the homogenate in the group to be tested and the homogenate in the blank control group wherein the amount of the homogenates is equivalent, and separately performing centrifugal separation to obtain supernatants; mixing the supernatants with the acid solution according to a certain proportion (a volume ratio of 1 to 19) to obtain supernatant diluents; mixing the supernatant diluents with the fluorescent enhancement liquid according to a certain proportion (a volume ratio of 1 to 199) to obtain mixed liquid; determining the fluorescent intensity of the mixed liquid at the specific emission wavelength under the specific excitation wavelength; recording the fluorescent intensity value of the mixed liquid in the group to be tested as $y_1$ and the fluorescent intensity value of the mixed liquid in the blank control group as $y_0$, and calculating the fluorescent intensity value (T) of the tissue per unit mass or volume according to the following formula:

$$T = \frac{y-B}{W},$$

wherein T is the fluorescent intensity value (cps/g or cps/mL) of the tissue per unit mass or volume; y is the fluorescent intensity value (cps) in the group to be tested or in the blank control group; and W is the weight (a solid block tissue, g) or the volume (a liquid tissue, mL) of the biological tissue samples. Significant difference analysis is performed on the T value. When P is greater than or equal to 0.05, it is indicated that significant difference does not exist between the group to be tested and the blank control group, and it is determined that the group to be tested excludes RE-nCaP (the content of the RE-nCaP is 0); and when P is smaller than 0.05, it is indicated that the significant difference exists between the group to be tested and the blank control group, continuing executing the step (c) and the step (d) to determine the content of the RE-nCaP in the group to be tested.

According to the scheme, the specific method of the step (c) comprises the following steps: uniformly mixing an Eu-nCaP aqueous suspension of a certain concentration (0.25 μg/mL) with the homogenate in the blank control group and the acid solution according to a certain proportion (a volume ratio of 1.52 to 1) separately, allowing the obtained mixtures to stand for a period of time (about 4 h), performing centrifugal separation to obtain supernatants, mixing the supernatants with the acid solution according to a certain proportion (a volume ratio of 1 to 19) to obtain supernatant diluents, mixing the supernatant diluents with the fluorescent enhancement liquid according to a certain proportion (a volume ratio of 1 to 199) to obtain test liquid, and determining the fluorescent intensity of the test liquid at the specific emission wavelength under the specific excitation wavelength; recording the fluorescent intensity of the homogenate in the blank control group as $A_1$ (cps), recording the fluorescent intensity of the acid solution as $A_0$ (cps), and calculating the tissue retention rate S per unit mass or volume according to the two fluorescent intensity according to the following formula:

$$S = \frac{(A_0 - A_1)}{A_0 W_0}$$

wherein S is the tissue retention rate per unit mass or volume and is dimensionless, and $W_0$ is the weight or the volume (g or mL) of the biological tissue in the blank control group; and calculating the tissue extraction rate R in the group to be tested according to the following formula through the tissue retention rate S per unit mass or volume:

$$R = (1 - S \cdot W_1) \times 100\%,$$

wherein R is the tissue extraction rate and is dimensionless, and $W_1$ is the weight or the volume (g or mL) of the tissue samples in the group to be tested.

According to the above scheme, in the step (d), the content M of RE-nCaP in the biological tissue samples of the group to be tested is calculated according to the following formula:

$$M = (T_1 - \overline{T_0}) \cdot \frac{kV}{RN},$$

wherein the unit of M is nmol/g or nmol/mL, $T_1$ is the fluorescent intensity value (cps/g or cps/mL) of the tissue per unit mass or unit volume in the group to be tested, $\overline{T_0}$ is the average value (cps/g or cps/mL) of the fluorescent intensity of the tissue per unit mass or unit volume of the blank control group, k is the ratio of the dilution ratio (the dilution ratio of tissue homogenate to the test liquid) to the mole content of rare earth elements in calcium phosphate, and V is the volume (L) of the homogenate in the group to be tested.

According to the scheme, the rare earth ions are specifically $Eu^{3+}$ or $Tb^{3+}$, and a rare earth ion doping manner is separate doping or codoping with other rare-earth elements.

According to the scheme, the value range of the molar ratio of RE/(RE+Ca) in the RE-nCaP is 0.1%-18%.

According to the above scheme, the acid solution is specifically a nitric acid aqueous solution or a hydrochloric acid aqueous solution, and the concentration of the acid solution is 0.5-5 mol/L.

According to the above scheme, the biological tissue samples in the group to be tested and the biological tissue samples in the control group are selected from blood, hearts, livers, spleens, lungs, kidneys, pancreases, brains, lymph, skeletons, skins, nerves, tumors and the like of animals (such as mice, rabbits and dogs) or people, or excrement (including urine and feces) of the animals and people.

Based on the characteristics that the rare earth ions can be doped into the nCaP structure, have stable fluorescent characteristics and do not have radioactive harm to organisms, the rare earth ions are extracted out by dissolving RE-nCaP in an acid (such as nitric acid or hydrochloric acid), and the concentration of the rare earth ions is calculated out through combination of the fluorescent intensity-concentration standard curve of the rare earth ions, and finally through combination of the fluorescent intensity value ($T_1$) of the tissue per unit mass or volume in the group to be tested, the average value ($T_0$) of the fluorescent intensity of the tissue per unit mass or unit volume in the blank control group, the tissue extraction rate (R), the dilution ratio of the sample homogenate to the test liquid, and the mole content of the rare earth ions in the calcium phosphate, the quantitative detection of the RE-nCaP in the biological tissue is realized.

Compared with the prior art, the beneficial effects of the quantitative detection method disclosed by the invention are mainly reflected in the following several respects: (1) based on quantitative detection of fluorescent rare earth ions contained in the RE-nCaP, the quantitative detection of the RE-nCaP in various biological tissues and excrement can be realized; (2) the accuracy is high, the detection limit is low (0.1 nmol/L), few samples (about 10 μL) required for detection are needed, and the detection cycle is short; and (3) the quantitative detection method is safe and pollution-free. The quantitative detection method belongs to a novel detection method which is safe and efficient and can be performed under normal conditions.

DETAILED DESCRIPTION OF THE INVENTION

In order to enable those skilled in the art to sufficiently understand the technical scheme and the beneficial effects of the quantitative detection method disclosed by the invention, further description is performed through combination with concrete embodiments.

The molar ratio of europium ion doped hydroxylapatite nanoparticles (Eu-nCaP, Eu/(Eu+Ca) used in the quantitative detection method disclosed by the invention is 4%, and the chemical molecular formula is $Eu_{0.4}Ca_{9.6}(PO_4)_6(OH)_2$. The europium ion doped hydroxylapatite nanoparticles are prepared according to a method disclosed by the Chinese patent CN105018086A (rare earth doped calcium phosphate fluorescent nanoparticles and preparation method thereof, Hanyingchao, et al), the Chinese patent CN107573938A (preparation method and application of rare earth doped apatite fluorescent nanometer points, Hanyingchao, et al). Other rare earth ion (such as Tb) doped calcium phosphate nanoparticles can also be prepared by the method.

The biological tissue samples (livers, kidneys, pancreases, hearts, blood, tumors and the like) involved by the invention all come from nude mice, and all nude mouse experiments are all strictly executed according to Regulations for the Administrations of Affairs Concerning Experimental Animals in China and the regulations of relevant international laws and regulations. In embodiments 1-5, normal nude mice of which the weight is about 20 g are used for experiments, in embodiment 6, nude mice (of which the weight is about 20 g) having a subcutaneous transplanted tumor model (HepG2 cells) are used for experiments, and the size of the tumors is 200-300 $mm^3$. In each embodiment, 6 nude mice in the same batch are used, and are randomly divided into 2 groups which are recorded as the group to be tested (an experimental group) and the blank control group. The fluorescent enhancement liquid used in the quantitative detection method disclosed by the invention is the DEL-FIA® Enhancement Solution, and the manufacturer is PerkinElmer Inc.

Figure 1:
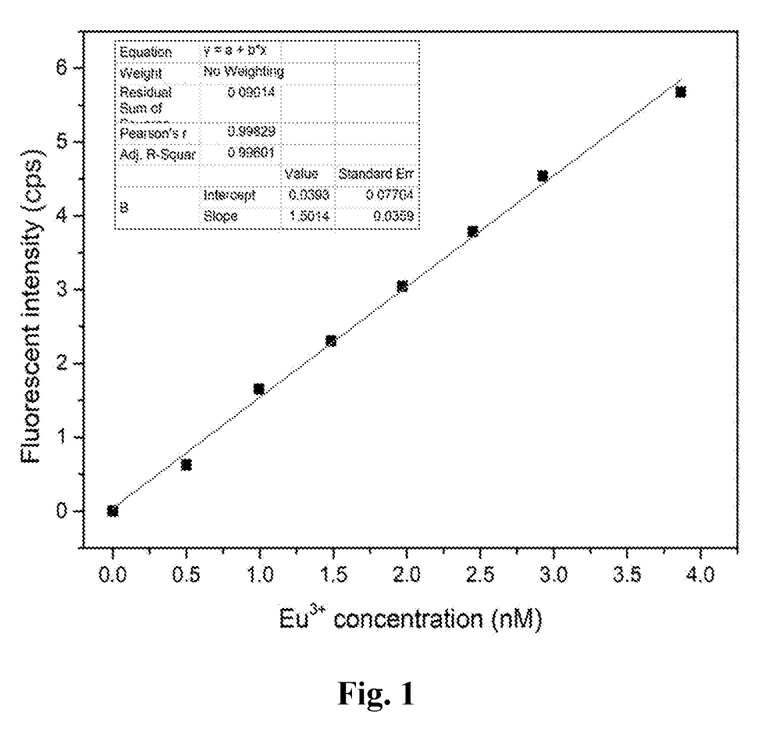
FIG. 1 is the fluorescent intensity-concentration standard curve of Eu ions established in the quantitative detection method disclosed by the invention.

The method for establishing the fluorescent intensity-concentration standard curve of rare earth ions disclosed by the invention specifically comprises the following steps of precisely weighing 36.641 mg of europium chloride hexahydrate, and dissolving the weighed europium chloride hexahydrate in 100 mL of ultra pure water to obtain europium ion storing liquid of which the concentration is 1 mmol/L; diluting the europium ion storing liquid into europium ion solutions of different concentrations (0.50000, 0.99502, 1.48522, 1.97044, 2.45098, 2.92654 and 3.86473, nmol/L) with the fluorescent enhancement liquid, and then determining the fluorescent intensity of the europium ion solutions of different concentrations at 618 nm under the condition that the excitation wavelength is 340 nm with the fluorescent spectrophotometer; and drawing the relationship curve of the fluorescent intensity y and the concentration x in a rectangular coordinate system, and performing linear fitting so as to obtain y=B+Nx ($R^2$=0.9960), wherein B is intercept (cps), the value of the intercept is 0.039, N is slope (cps/(nmol/L)), the value of the slope is 1.501, and the result is as shown in the FIG. 1. The standard curve is uniformly used in all embodiments in the invention.

Embodiment 1

An Eu-nCaP aqueous suspension (200 µL, 5 mg/mL) is injected into the nude mice in the group to be tested through caudal vein injection, and timing immediately starts. The nude mice in the blank control group are not subjected to injection treatment. 8 h later, the liver tissues of the nude mice in the group to be tested and the liver tissues of the nude mice in the blank control group are taken out and are thoroughly rinsed with a PBS solution, and 3 liver samples are obtained in each group (namely that 3 liver samples are obtained in the group to be tested, and 3 liver samples are obtained in the blank control group). After surface moisture is thoroughly absorbed with paper, the weight W(g) of each liver sample is weighed, wherein $W_1$ in the group to be tested is sequentially 0.097 g, 0.070 g and 0.074 g, and $W_0$ in the blank control group is sequentially 0.054 g, 0.102 g and 0.085 g. The tissue samples of the group to be tested and the blank control group are prepared into 1 mL of liver homogenate with 2 mol/L nitric acid. 0.5 mL of the liver homogenate in the group to be tested and 0.5 mL of the liver homogenate in the blank control group are separately taken, and are put in centrifugal tubes, high speed centrifugation (5000 r/min) is performed, 40 µL of supernatant and 760 µL of nitric acid (2 mol/L) are mixed so that a supernatant diluent is prepared. 5 µL of the supernatant diluent and 995 µL of fluorescent enhancement liquid are mixed so that mixed liquid is prepared, and the fluorescent intensity of the mixed liquid at the emission wavelength of 618 nm (Ex=340 nm) is tested. The fluorescent intensity value $y_1$ in the group to be tested is sequentially 10.068 cps, 11.244 cps and 10.463 cps, and the fluorescent intensity value $y_0$ in the blank control group is sequentially 0.780 cps, 0.080 cps and 0.653 cps. The fluorescent intensity value (T) of the livers per unit mass in the group to be tested and the blank control group is calculated according to the formula (I):

$$T = \frac{y - B}{W},$$  (I)

Figure 2:
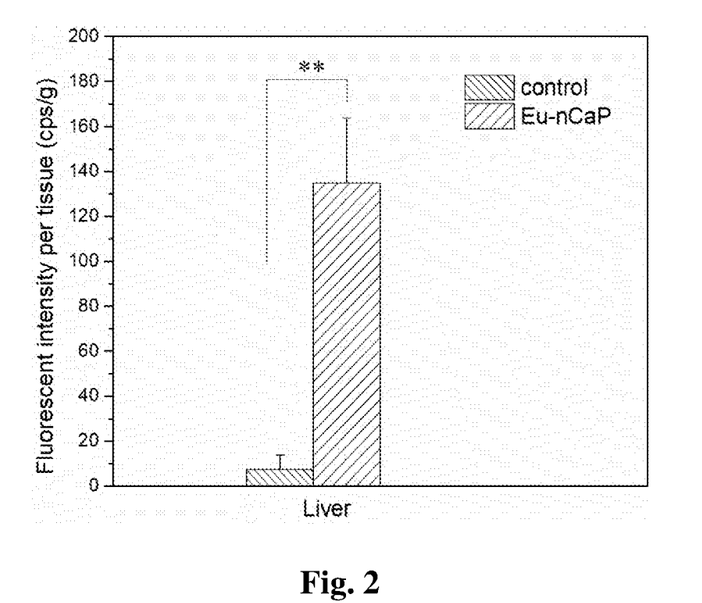
FIG. 2 is the detection result of the fluorescent intensity value of the livers per unit mass in the group to be tested and the blank control group in the embodiment 1.

The fluorescent intensity value $T_1$ of the livers per unit mass in the group to be tested is sequentially 103.392 cps/g, 160.071 cps/g and 140.865 cps/g, and the fluorescent intensity value $T_0$ of the livers per unit mass in the blank control group is sequentially 13.722 cps/g, 0.402 cps/g and 7.224 cps/g; through single factor variance analysis, compared with the $T_0$ value in the blank control group, the $T_1$ value in the group to be tested has significance difference (P=0.0017<0.05), and the result is seen in the FIG. 2. It can be seen that the content of Eu-nCaP in the biological tissue samples in the group to be tested is determined through subsequent steps.

The extraction rate of the Eu-nCaP in the livers is calculated through the following steps: separately putting the homogenate in the blank control group and nitric acid (2 mol/L) having the same volume (500 µL) as that of the homogenate in the blank control group in the centrifugal tubes, separately adding 760 µL of Eu-nCaP suspension liquid (0.25 µg/mL), performing uniform mixing, allowing the mixtures to stand for 4 h, and performing centrifuging; taking 40 µL, of supernatants and 760 µL of nitric acid (2 mol/L), and performing mixing to obtain supernatant diluents; taking 5 µL of the supernatant diluent and 995 µL of the fluorescent enhancement liquid, and performing mixing so as to obtain test liquid; testing the fluorescent intensity of the test liquid at the emission wave length of at 618 nm (Ex=340 nm), wherein the fluorescent intensity $A_1$ of the homogenate in the blank control group is 2.375 cps, and the fluorescent intensity $A_0$ in a nitric acid group is 2.421 cps, and calculating the tissue retention rate S per unit mass according to the formula (II):

$$S = \frac{(A_0 - A_1)}{A_0 W_0},$$  (II)

Based on the calculated S=0.085, further calculating the tissue extraction rate R according to the formula (III):

$$R = (1 - S \cdot W_1) \times 100\%,$$  (III)

so that the liver extraction rate R in 3 groups to be tested is 97.8%, 98.4% and 98.3% sequentially. The content of the Eu-nCaP in the livers in the group to be tested is calculated through the following steps of according to the known fluorescent intensity-concentration standard curve, the fluorescent intensity value ($T_1$) of the livers per unit mass in the group to be tested, the average value ($\overline{T_0}$) of the fluorescent intensity value of the livers per unit mass in the blank control group, the dilution ratio of the sample homogenate to the test liquid, the liver extraction rate and the chemical molecular formula of europium doped hydroxylapatite, and calculating the content M of Eu-nCaP in the liver tissue of the group to be tested according to the formula (IV):

$$M = (T_1 - \overline{T_0}) \cdot \frac{kV}{RN},$$  (IV)

wherein in the embodiment, k is 4000/0.4=$10^4$, V=1*$10^{-3}$ L, and $\overline{T_0}$=7.116; the content of the Eu-nCaP in the liver tissue of the group to be tested is calculated to be 655.627 nmol/g, 1035.222 nmol/g and 906.053 nmol/g respectively; and therefore, the content of the Eu-nCaP in the liver tissue in the group to be tested is 865.634±192.999 nmol/g.

Embodiment 2

The kidneys of the nude mice in the group to be tested and the kidneys of the nude mice in the control group are obtained by the method in the embodiment 1, and 3 samples are contained in each group (3 samples are contained in the group to be tested, and 3 samples are contained in the blank control group); the weight W(g) of each kidney sample is weighed through a scales, wherein $W_1$ in the group to be tested is sequentially 0.073 g, 0.054 g and 0.065 g, and $W_0$ in the blank control group is sequentially 0.020 g, 0.161 g and 0.097 g; and the tissue samples of the group to be tested and the blank control group are prepared into 1 mL of kidney homogenate through the 2 mol/L nitric acid.

Figure 3:
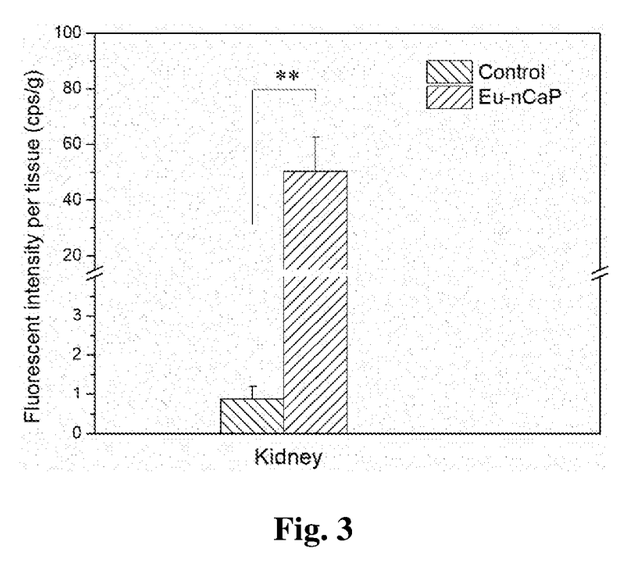
FIG. 3 is the detection result of the fluorescent intensity value of the kidneys per unit mass in the group to be tested and the blank control group in the embodiment 2.

By the method in the embodiment 1, the kidney homogenate in the group to be tested and the kidney homogenate in the blank control group are prepared into mixed liquid, the fluorescent intensity value y of the mixed liquid is tested, the fluorescent intensity value $y_1$ in the group to be tested is sequentially 4.555 cps, 2.822 cps and 2.498 cps, and the fluorescent intensity value $y_0$ in the blank control group is sequentially 0.282 cps, 0.174 cps and 0.095 cps; through the formula (I), the $T_1$ value in the group to be tested is calculated out to be 61.863 cps/g, 51.537 cps/g and 37.831 cps/g sequentially, and the $T_0$ value in the blank control group is calculated out to be 1.215 cps/g, 0.839 cps/g and 0.577 cps/g sequentially; through single factor variance analysis, compared with the $T_0$ value in the blank control group, the $T_1$ value in the group to be tested has significant difference (P=0.0021<0.05), and the result is seen in the FIG. 3; and it can be seen that the content of the Eu-nCaP in the group to be tested is further calculated through subsequent steps.

According to the method in the embodiment 1, the fluorescent intensity value of the homogenate in the blank control group and the fluorescent intensity value of the nitric acid are tested, the retention rate S is calculated according to the formula (II), and further the extraction rate R of the Eu-nCaP in the kidneys is calculated according to the formula (III), wherein $A_1$=2.279 cps, $A_0$=2.421 cps and $W_0$=0.097 g; and therefore, the kidney extraction rate R in the 3 groups to be tested is calculated to be 95.6%, 96.7% and 96.1%.

The content of the Eu-nCaP in the kidneys in the group to be tested is calculated through the following step: according to the formula (IV) (in the embodiment, B=0.039, N=1.501, V=1*$10^{-3}$L, k=$10^4$, $T_0$=0.877), calculating the content of the Eu-nCaP in the kidneys in the group to be tested to be 425.065, 348.901 and 256.267 nmol/g respectively, thereby obtaining the content of the Eu-nCaP in the kidney tissue of the group to be tested being 343.411±84.533 nmol/g.

Embodiment 3

The pancreases of the nude mice in the group to be tested and the pancreases of the nude mice in the control group are obtained by the method in the embodiment 1, and 3 samples are contained in each group (3 samples are contained in the group to be tested, and 3 samples are contained in the blank control group); the weight W(g) of each pancrease sample is weighed through a scales, wherein $W_1$ in the group to be tested is sequentially 0.027 g, 0.029 g and 0.028 g, and $W_0$ in the blank control group is sequentially 0.050 g, 0.033 g and 0.034 g; and the tissue samples in the group to be tested and the blank control group are prepared into 1 mL of pancrease homogenate through the 2 mol/L nitric acid.

Figure 4:
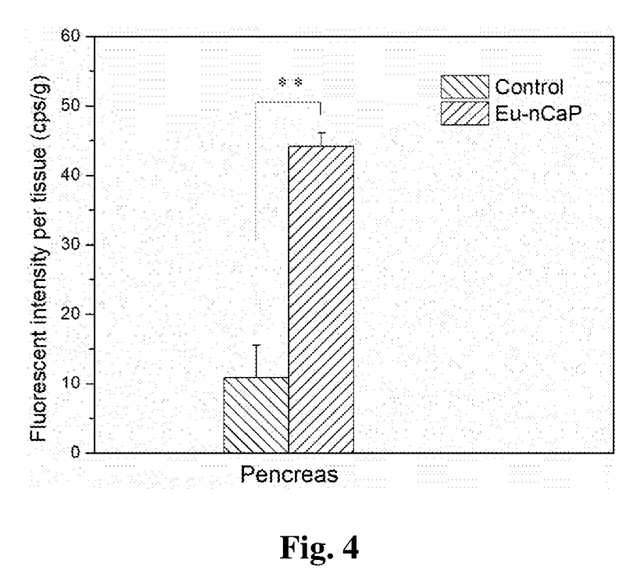
FIG. 4 is the detection result of the fluorescent intensity value of the pancreases per unit mass in the group to be tested and the blank control group in the embodiment 3.

According to the method in the embodiment 1, the pancrease homogenate the group to be tested and the pancrease homogenate in the blank control group are prepared into mixed liquid, the fluorescent intensity value of the mixed liquid is tested, the fluorescent intensity value $y_1$ in the group to be tested is sequentially 1.245 cps, 1.256 cps and 1.320 cps, and the fluorescent intensity value $y_0$ in the blank control group is sequentially 0.312 cps, 0.491 cps and 0.495 cps; through the formula (I), the $T_1$ value in the group to be tested is calculated to be 44.667, 41.966, 45.750 cps/g sequentially, and the $T_0$ value in the blank control group is calculated to be 5.460, 13.679, 13.412 cps/g sequentially; through single factor variance analysis, compared with the $T_0$ value in the blank control group, the $T_1$ value in the group to be tested has significant difference (P=0.0003<0.05), and the result is seen in the FIG. 4; and it can be seen that the content of the Eu-nCaP in the group to be tested is further determined through subsequent steps.

According to the method in the embodiment 1, the fluorescent intensity value of the homogenate in the blank control group and the fluorescent intensity value of the nitric acid are tested, the retention rate S is calculated according to the fluorescent intensity value, and the extraction rate R of the Eu-nCaP in the pancreases is further calculated, wherein $A_1$=2.032 cps, $A_0$=2.421cps and $W_0$=0.050 g; and therefore, the pancrease extraction rate R in the 3 groups to be tested is calculated to be 91.32%, 90.68% and 91.00% from the formula (III).

The content of the Eu-nCaP in the pancreases in the group to be tested is calculated through the following step: according to the formula (IV) (in the embodiment, B=0.039, N=1.501, V=1*$10^{-3}$, k=$10^4$, $T_0$3210.856), calculating the content of the Eu-nCaP in the kidneys in the group to be tested to be 246.656 nmol/g, 228.559 nmol/g and 255.458 nmol/g respectively, thereby obtaining the content of the Eu-nCaP in the pancrease tissue of the group to be tested being 243.557±13.715 nmol/g.

Embodiment 4

Reference to the method in the embodiment 1, 0.04 mL (W) of blood of the nude mice in the group to be tested and 0.04 mL (W) of blood of the nude mice in the control group are separately collected, and the blood of the nude mice in the group to be tested and 1 mL of nitric acid (2 mol/L) are mixed and uniformly shaken, the blood of the nude mice in the control group and 1 mL of nitric acid (2 mol/L) are mixed and uniformly shaken, so that blood homogenates are prepared. 3 samples are contained in each group (3 samples are contained in the group to be tested, and 3 samples are contained in the blank control group).

Figure 5:
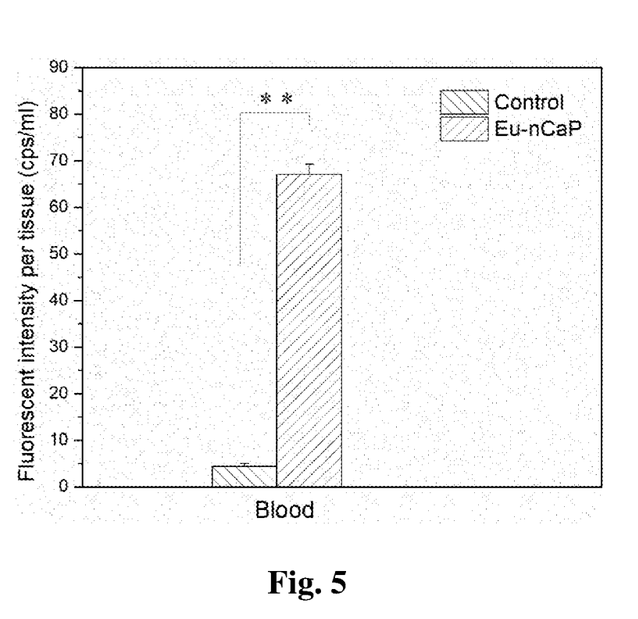
FIG. 5 is the detection result of the fluorescent intensity value of the blood per unit volume in the group to be tested and the blank control group in the embodiment 4.

According to the method in the embodiment 1, the fluorescent intensity of the blood homogenate in the group to be tested and the blood homogenate in the blank control group are tested, the fluorescent intensity $y_1$ in the group to be tested is sequentially 2.642 cps, 2.720 cps and 2.810 cps, and the fluorescent intensity value $y_0$ in the blank control group is sequentially 0.210 cps, 0.241 cps and 0.196 cps; through the formula (I), the $T_1$ value in the group to be tested is calculated to be 65.075, 67.025, 69.275 cps/mL sequentially, and the $T_0$ value in the blank control group is calculated to be 4.275, 5.050, 3.925 cps/mL sequentially; through single factor variance analysis, compared with the $T_0$ value in the blank control group, the $T_1$ value in the group to be tested has significant difference (P=0.000001<0.05), and the result is seen in the FIG. 5; and it can be seen that the content of the Eu-nCaP in the group to be tested is further determined through subsequent steps.

According to the method in the embodiment 1, the fluorescent intensity value of the homogenate in the blank control group and the fluorescent intensity value of the nitric acid is tested, the retention rate S is calculated according to the fluorescent intensity value, and the extraction rate R of the Eu-nCaP in the blood is further calculated, wherein $A_1$=2.323 cps, $A_0$=2.421 cps and $W_0$=0.04 mL; and therefore, the blood extraction rate R in the 3 groups to be tested is calculated from the formula (III) to be 98.9%.

The content of the Eu-nCaP in the blood in the group to be tested is calculated through the following step: according to the formula (IV) (in the embodiment, B=0.039, N=1.501, V=1*$10^{-3}$, k=$10^4$, $T_0$=4.417), calculating the content of the Eu-nCaP in the blood in the group to be tested to be 409.026 nmol/mL, 422.175 nmol/mL and 437.347 nmol/mL respectively, thereby obtaining the content of the Eu-nCaP in the blood tissue of the group to be tested being 422.849±14.173 nmol/mL.

Embodiment 5

The hearts of the nude mice in the group to be tested and the hearts of the nude mice in the control group are obtained by the method in the embodiment 1, and 3 samples are contained in each group (3 samples are contained in the group to be tested, and 3 samples are contained in the blank control group); the weight W(g) of each heart sample is weighed through a scales, wherein $W_1$ in the group to be tested is sequentially 0.027 g, 0.024 g and 0.012 g, and $W_0$ in the blank control group is sequentially 0.018 g, 0.063 g and 0.020 g; and the tissue samples in the group to be tested and the blank control group are prepared into 1 mL of heart homogenate through the 2 mol/L nitric acid.

Figure 6:
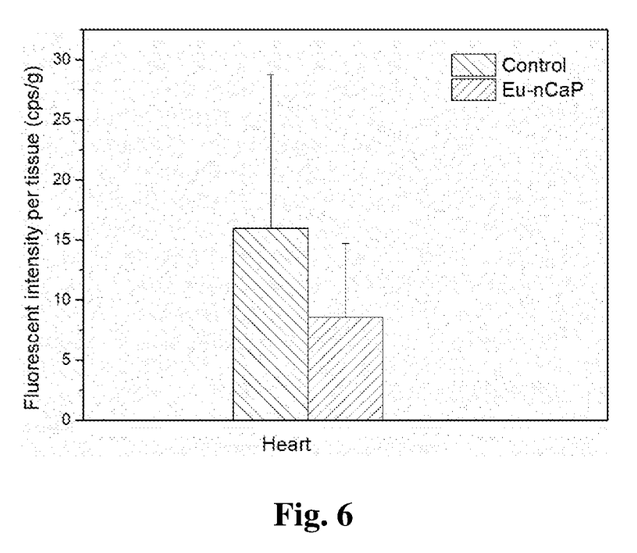
FIG. 6 is the detection result of the fluorescent intensity value of the hearts per unit weight in the group to be tested and the blank control group in the embodiment 5.

According to the method in the embodiment 1, the heart homogenate in the group to be tested and the heart homogenate in the blank control group are prepared into mixed liquid, the fluorescent intensity value of the mixed liquid is tested, the fluorescent intensity value $y_1$ in the group to be tested is sequentially 0.133 cps, 0.410 cps and 0.120 cps, and the fluorescent intensity value $y_0$ in the blank control group is sequentially 0.475cps, 0.117cps and 0.487cps; through the formula (I), the $T_1$ value in the group to be tested is calculated to be 3.443, 15.394, 6.750 cps/g sequentially, and the $T_0$ value in the blank control group is calculated to be 24.222, 1.238, 22.400 cps/g sequentially; through single factor variance analysis, P=0.416>0.05, indicating that compared with the $T_0$ value in the blank control group, the $T_1$ value in the group to be tested has no significant difference, and the result is seen in the FIG. 6; and therefore, the content of the Eu-nCaP in the heart tissue is determined to be 0 nmol/g.

Embodiment 6

The tumor tissue of the nude mice in the group to be tested and the tumor tissue of the nude mice in the control group are obtained by the method in the embodiment 1, and 3 samples are contained in each group (3 samples are contained in the group to be tested, and 3 samples are contained in the blank control group); the weight W(g) of each tumor sample is weighed through a scales, wherein $W_1$ in the group to be tested is sequentially 0.037 g, 0.027 g and 0.026 g, and $W_0$ in the blank control group is sequentially 0.037 g, 0.115 g and 0.022 g; and the tissue samples in the group to be tested and the blank control group are prepared into 1 mL of tumor homogenate through the 2 mol/L nitric acid.

Figure 7:
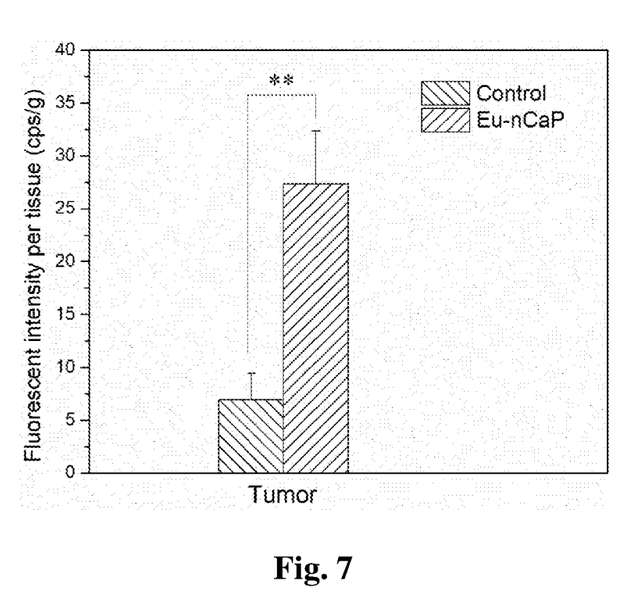
FIG. 7 is the detection result of the fluorescent intensity value of the tumors per unit mass in the group to be tested and the blank control group in the embodiment 6.

According to the method in the embodiment 1, the tumor homogenate in the group to be tested and the tumor homogenate in the blank control group are prepared into mixed liquid, the fluorescent intensity value of the mixed liquid is tested, the fluorescent intensity value $y_1$ in the group to be tested is sequentially 0.848, 0.810 and 0.861 cps, and the fluorescent intensity value $y_0$ in the blank control group is sequentially 0.368, 0.516 and 0.210 cps; through the formula (I), the $T_1$ value in the group to be tested is calculated to be 21.865 cps/g, 28.556 cps/g and 31.615 cps/g sequentially, and the $T_0$ value in the blank control group is calculated to be 8.892 cps/g, 4.148 cps/g and 7.773cps/g sequentially; through single factor variance analysis, compared with the $T_0$ value in the blank control group, the $T_1$ value in the group to be tested has significant difference (P=0.0032<0.01), and the result is seen in the FIG. 7; and it can be seen that the content of the Eu-nCaP in the group to be tested is further determined through subsequent steps.

According to the method in the embodiment 1, the fluorescent intensity value of the homogenate in the blank control group and the fluorescent intensity value of the nitric acid are tested, the retention rate S is calculated according to the fluorescent intensity value, and further the extraction rate R of the Eu-nCaP in the tumors is calculated, wherein $A_1$=2.323 cps, $A_0$=2.421 cps and $W_0$=0.115 g; and therefore, the tumor extraction rate R in the 3 groups to be tested is calculated from the formula (III) to be 98.70%, 99.05% and 99.08%.

The content of the Eu-nCaP in the tumors in the group to be tested is calculated through the following step: according to the formula (IV) (in the embodiment, B=0.039, N=1.501, V=1*10$^{-3}$, k=10$^4$, $T_0$=6.937), calculating the content of the Eu-nCaP in the group to be tested to be 100.765 nmol/g, 145.410 nmol/g and 165.932 nmol/g respectively, thereby obtaining the content of the Eu-nCaP in the tumor tissue of the group to be tested being 137.369±33.319 nmol/g.

What is claimed is:

1. A quantitative detection method of rare earth doped calcium phosphate fluorescent nanoparticles (RE-nCaP) in at least one biological tissue of one of blood, heart, liver, spleen, lung, kidney, pancreas, brain, lymph, skin, and nerve of an animal, comprising steps of:
(a) establishing a fluorescent intensity-concentration standard curve of rare earth (RE) ions in a fluorescent enhancement liquid, wherein the fluorescent intensity-concentration standard curve satisfies a relationship of Y=B+N·X, wherein Y and X are respectively a fluorescent intensity and an RE concentration of the fluorescent enhancement liquid, and B and N are constants and respectively an intercept and a slope of the fluorescent intensity-concentration standard curve;
(b) separately treating at least one test biological tissue sample of a group to be tested, and at least one control biological tissue sample of a blank control group with an acid solution to obtain homogenates of the group to be tested and the blank control group, wherein the at least one test biological tissue sample of the group to be tested is obtained from said at least one biological tissue of the animal, and the at least one control biological tissue sample of the blank control group is obtained from at least one control biological tissue of another animal containing no RE-nCaP, wherein said at least one control biological tissue is a tissue of one of blood, heart, liver, spleen, lung, kidney, pancreas, brain, lymph, skin, and nerve of said another animal that is corresponding to said one of said blood, heart, liver, spleen, lung, kidney, pancreas, brain, lymph, skin, and nerve of the animal;
performing centrifugal separation on the homogenates of the at least one test biological tissue sample of the group to be tested and the at least one control biological tissue sample of the blank control group separately to obtain supernatants of the at least one test biological tissue sample of the group to be tested and the at least one control biological tissue sample of the blank control group;
diluting the supernatants of the at least one test biological tissue sample of the group to be tested and the at least one control biological tissue sample of the blank control group with the fluorescent enhancement liquid;
detecting fluorescent intensities of the diluted supernatants of the at least one test biological tissue sample of the group to be tested and the at least one control biological tissue sample of the blank control group;
calculating values, T and $T_0$, of a fluorescent intensity per unit mass or volume of the at least one test biological tissue sample of the group to be tested and the at least one control biological tissue sample of the blank control group according to formula (I):

$$T = \frac{y - B}{W}; \text{ and } T_0 = \frac{y_0 - B}{W_0} \quad \text{(I)}$$

wherein y and $y_0$ are respectively the detected fluorescent intensities of the diluted supernatants of the at least one test biological tissue sample of the group to be tested and the at least one control biological tissue sample of the blank control group, W is a weight or volume of the at least one test biological tissue sample of the group to be tested, and $W_0$ is a weight or volume of the at least one control biological tissue sample of the blank control group;

performing significant difference analysis on the values T and $T_0$ of the fluorescent intensity per unit mass or volume between the at least one test biological tissue sample of the group to be tested and the at least one control biological tissue sample of the blank control group, so as to determine if the at least one test biological tissue sample in the group to be tested contain the RE-nCaP; and continuing to perform a step (c) and a step (d) to further determine an amount of the RE-nCaP when the at least one test biological tissue sample in the group to be tested are determined to contain the RE-nCaP;

(c) separately adding the RE-nCaP to the homogenate of the at least one control biological tissue sample of the blank control group and to the acid solution having a same volume as that of the homogenate of the at least one control biological tissue sample of the blank control group;

performing centrifugal separation on the RE-nCaP added homogenate of the at least one control biological tissue sample of the blank control group and the RE-nCaP added acid solution separately to obtain supernatants of the RE-nCaP added homogenate of the at least one control biological tissue sample of the blank control group and the RE-nCaP added acid solution;

diluting the supernatants of the RE-nCaP added homogenate of the at least one control biological tissue sample of the blank control group and the RE-nCaP added acid solution with the fluorescent enhancement liquid;

detecting fluorescent intensities of the diluted supernatants of the RE-nCaP added homogenate of the at least one control biological tissue sample of the blank control group and the RE-nCaP added acid solution;

calculating a tissue retention rate, S, per unit mass or volume according to formula (II):

$$S = \frac{(A_0 - A_1)}{A_0 W_0} \quad \text{(II)}$$

wherein $A_1$ is the detected fluorescent intensity of the RE-nCaP added homogenate of the at least one control biological tissue sample of the blank control group and $A_0$ is the detected fluorescent intensity of the RE-nCaP added acid solution, and $W_0$ is the weight or volume of the at least one control biological tissue sample of the blank control group; and calculating a tissue extraction rate, R, of the group to be tested according to a weight or volume of the at least one test biological tissue sample in the group to be tested according to formula (III):

$$R = (1 - S \cdot W) \times 100\% \quad \text{(III)}$$

wherein W is the weight or volume of the at least one test biological tissue sample in the group to be tested; and (d) calculating an amount, M, of the RE-nCaP in the at least one test biological tissue sample of the group to be tested according to formula (IV):

$$M = (T_1 - \overline{T_0}) \cdot \frac{kV}{RN} \quad \text{(IV)}$$

wherein $T_1$ is the value of the fluorescent intensity per unit mass or volume of the at least one test biological tissue sample of the group to be tested, $\overline{T_0}$ is an average value of the fluorescent intensity per unit mass or volume of the at least one control biological tissue sample of the blank control group, k is a ratio of a dilution ratio of the homogenate of the at least one test biological tissue sample to the diluted supernatants of the at least one test biological tissue sample to a mole amount of rare earth elements in calcium phosphate, V is a homogenate volume of the at least one test biological tissue sample in the group to be tested, and R is the tissue extraction rate R of the group to be tested.

2. The method according to claim 1, wherein the step (a) of establishing the fluorescent intensity-concentration standard curve comprises:

by using the fluorescent enhancement liquid as a solvent, preparing a series of rare earth ion standard solutions of different concentrations;

determining fluorescent intensities of the rare earth ion standard solutions at a specific emission wavelength under a specific excitation wavelength by a fluorescent spectrophotometer; and performing fitting of the determined fluorescent intensities and the different concentrations of the rare earth ion standard solutions so as to obtain the fluorescent intensity-concentration standard curve.

3. The method according to claim 1, wherein in the step (b), said separately treating the at least one test biological tissue sample of the group to be tested, and the at least one control biological tissue sample of the blank control group with the acid solution comprises:

measuring a mass or volume of the at least one test biological tissue sample in the group to be tested and a mass or volume of the at least one control biological tissue sample in the blank control group separately;

adding the acid solution to the at least one test biological tissue sample in the group to be tested and the at least one control biological tissue sample in the blank control group separately to obtain the homogenates of the group to be tested and the blank control group;

taking an amount of the homogenate in the group to be tested and an amount of the homogenate in the blank control group, wherein the amount of the homogenate in the group to be tested and the amount of the homogenate in the blank control group are equivalent;

said diluting the supernatants of the group to be tested and the blank control group with the fluorescent enhancement liquid comprises:

mixing the supernatants of the group to be tested and the blank control group with the acid solution according to a proportion to obtain supernatant diluents of the group to be tested and the blank control group, respectively;

mixing the supernatant diluents of the group to be tested and the blank control group with the fluorescent enhancement liquid according to a proportion to obtain mixed liquids of the group to be tested and the blank control group, respectively; and said performing the significant difference analysis on the values T and $T_0$ of the fluorescent intensities per unit mass or volume between the at least one test biological tissue sample of the group to be tested and the at least one control biological tissue sample of the blank control group comprises:

when P is greater than or equal to 0.05, indicating that significant difference does not exist between the at least one test biological tissue sample in the group to be tested and the at least one control biological tissue sample in the blank control group, and determining that the at least one test biological tissue sample in the group to be tested does not contain the RE-nCaP; and when P is smaller than 0.05, indicating that the significant difference exists between the at least one test biological tissue sample in the group to be tested and the at least one control biological tissue sample in the blank control group, determining that the at least one test biological tissue sample in the group to be tested contains the RE-nCaP.

4. The method according to claim 1, wherein the rare earth ions are $Eu^{3+}$ or $Tb^{3+}$, and a rare earth ion doping manner is separate doping or codoping with other rare-earth elements.

5. The method according to claim 1, wherein a value range of a molar ratio of RE/(RE+Ca) in the RE-nCaP is 0.1%-18%.

6. The method according to claim 1, wherein the acid solution is a nitric acid aqueous solution or a hydrochloric acid aqueous solution, and a concentration of the acid solution is 0.5-5 mol/L.

7. The method according to claim 1, wherein a fluorescent intensity of a sample solution at a specific emission wavelength under a specific excitation wavelength is detected through a fluorescent spectrophotometer, the specific excitation wavelength is 330-350 nm, and the specific emission wavelength is 618 nm.

\* \* \* \* \*